United States Patent [19]

Pfaff et al.

[11] Patent Number: 4,681,936
[45] Date of Patent: Jul. 21, 1987

[54] PREPARATION OF SUGAR KETALS

[75] Inventors: Klaus-Peter Pfaff, Mannheim; Joachim Paust, Neuhofen; Horst Hartmann, Boehl-Iggelheim, all of Fed. Rep. of Germany

[73] Assignee: Basf Aktiengesellschaft, Ludwigshafen, Fed. Rep. of Germany

[21] Appl. No.: 826,317

[22] Filed: Feb. 5, 1986

[30] Foreign Application Priority Data

Feb. 15, 1985 [DE] Fed. Rep. of Germany ....... 3505150

[51] Int. Cl.$^4$ .............................................. C07H 1/00
[52] U.S. Cl. .................................. 536/124; 536/18.5; 536/120
[58] Field of Search ....................... 536/124, 120, 18.5

[56] References Cited

U.S. PATENT DOCUMENTS

| 3,607,862 | 9/1971 | Jaffe et al. | 536/124 |
| 4,460,767 | 7/1984 | Matsumura et al. | 536/124 |
| 4,464,204 | 8/1984 | Niekamp et al. | 536/124 |
| 4,464,530 | 8/1984 | Matsumura et al. | 536/124 |
| 4,465,521 | 8/1984 | Seidman et al. | 536/124 |

FOREIGN PATENT DOCUMENTS

| 138436 | 4/1985 | European Pat. Off. | 536/124 X |
| 139486 | 5/1985 | European Pat. Off. | 536/124 |

OTHER PUBLICATIONS

Synthesis of Methyl 4.6-O-Methylene-D-Glycopyranosides, J. C. Goodwin et al., Res. 28 (1973) pp. 213-219.
Die Starke; "A New Synthesis of Methyl-4,6-0-Propylidine-a-D-Glucopyranoside"; C. Boffi et al; 21 (1969) p. 100.
Die Starke; "A Novel Synthetic Approach to the Ylidene Derivatives of Carbohydrates; " E. Bergonzi et al. 16 (1964) pp. 386-390.

Primary Examiner—Johnnie R. Brown
Attorney, Agent, or Firm—Oblon, Fisher, Spivak, McClelland & Maier

[57] ABSTRACT

Sugar ketals are prepared by reacting a sugar with a ketone in the presence of an acid catalyst by a process in which A. a molecular boron trifluoride compound or trifluoromethanesulfonic acid is used in an amount of only from 0.01 to 10% by weight, based on the sugar used,
B. up to a 30-fold molar excess of the ketone is used and
C. the water formed during the reaction is removed continuously from the reaction mixture.

In a particularly advantageous embodiment of the process, the boron trifluoride is used in the form of boron trifluoride etherate and, when the reaction is complete, this compound or the trifluoromethanesulfonic acid is rendered ineffective under non-aqueous conditions, after which the ketone is evaporated off and the reaction mixture is then subjected to fractional distillation. The process is particularly important for the reaction of L-sorbose with acetone to obtain 2,3:4,6-di-O-isopropylidene-L-sorbofuranose, which is required for the synthesis of ascorbic acid.

14 Claims, No Drawings

PREPARATION OF SUGAR KETALS

The present invention relates to a process for the preparation of sugar ketals, in which the acid catalyst is employed in a catalytic amount.

Sugar ketals are sugar derivatives which are frequently synthesized when it is desired to protect the hydroxyl groups of the sugar. For example, 2,3:4,6-di-O-isopropylidene-α-L-sorbose (diacetone-L-sorbose) is an important intermediate in the preparation of vitamin C by the Reichstein method.

A very large number of different methods for the preparation of sugar ketals have been described. Various acid catalysts can be used for carrying out the reaction between the particular sugar and the ketone under thermodynamic control. These catalysts are on the one hand mineral acids, such as sulfuric acid, hydriodic acid, hydrobromic acid, hydrochloric acid, phosphoric acid or perchloric acid, and on the other hand acidic ion exchangers or organic acids, such as acetic acid and sulfonic acids. In addition Lewis acids or heavy metal salts may also be used. These include tin chloride, iron chloride, copper sulfate and other copper salts, as well as the chlorides of rare earth metals.

To achieve high conversions, it is necessary to bind or remove the water formed during the reaction. For this reason, for example, sulfuric acid is frequently used. The disadvantage here is that large amounts of acid must be employed, and have to be neutralized with an alkali at the end of the reaction, producing corresponding amounts of sulfates.

Hence, to simplify the working up procedure and disposal, methods have also been worked out in which only catalytic amounts of acid are used.

For example, German Laid-Open Application DOS 2,003,067 describes a process for the preparation of sugars in which a catalytic amount of perchloric acid, iron(III) chloride or iron(III) bromide is used as the catalyst. The water of reaction formed is removed by azeotropic distillation. European Patent Applications 76,118 and 91,223 describe the use of copper salts and hydriodic acid, respectively. The critical factors in some of these processes are the yields and the purities of the sugar ketals being synthesized. Only if the strength and amount of the acid catalyst used are chosen optimally is it possible to suppress the formation of troublesome by-products. The conventional processes have substantial disadvantages, especially for the preparation of 2,3:4,6-di-O-isopropylidene-α-L-sorbofuranose, which is required as an intermediate for the synthesis of vitamin C. For example, when heavy metals are used as catalysts, the presence of traces of catalyst may give rise to problems in the subsequent stages of the vitamin C synthesis.

The use of boron trifluoride etherate as a catalyst for the reaction of sugars with aldehydes and ketones in a suitable solvent, such as dimethyl sulfoxide or dioxane, has also been investigated (cf. E. Bergonzi et al., "Die Stärke" 16 (1964), 386–390, and C. Boffi et al., ibid 21 (1969) 100). In this procedure, good yields of sugar acetals were obtained only in the reaction with aldehydes. According to these publications, the method appears to be much less suitable for the reaction of sugars with ketones. This applies in particular to the reaction in dimethyl sulfoxide. However, even in the reaction of D-glucose with acetone in dioxane as a solvent, the desired ketal was obtained in a yield of only 20%, based on the sugar used, in spite of the fact that 2 equivalents of $BF_3$ etherate were employed. Moreover, the expensive procedure for removing the solvent is a decisive disadvantage of this process. In the reaction of methyl glycosides with formaldehyde (from 1,3,5-trioxane) using dioxane as a solvent and $BF_3$ etherate as a catalyst, the corresponding 4,6-O-methylene compounds were only obtained in a yield of less than 30% (cf. J. C. Goodwin et al., Carbohydr. Res. 28 (1973), 213–219).

It is an object of the present invention to improve the process for the preparation of sugar ketals, in particular for the preparation of diacetone-L-sorbose, which is important for the vitamin C synthesis, so that the reaction of sugars with ketones takes place with good yields and gives very pure products even in the absence of a heavy metal catalyst, and can be carried out in a simple manner in the presence of only a catalytic amount of an acid catalyst, and the reaction mixture can be worked up in a very simple manner.

We have found that this object is achieved and that, surprisingly, the reaction of sugars with suitable ketones in the presence of boron trifluoride diethyl etherate or trifluoromethanesulfonic acid as the acid catalyst gives good yields of sugar ketals if the reaction is carried out in the presence of only a catalytic amount, i.e. only from 0.01 to 10% by weight, based on the sugar used, of boron trifluoride diethyl etherate or trifluoromethanesulfonic acid, and the water formed during the reaction is removed continuously from the reaction mixture. It was also surprising that under these conditions, in particular in the reaction with acetone, it was possible to dispense with the use of a solvent, such as dioxane or dimethyl sulfoxide, which increases the solubility of the sugar. By using only a catalytic amount of the $BF_3$ compound or trifluoromethanesulfonic acid and dispensing with an additional solvent, subsequent working up of the reaction mixture can be carried out in a substantially simpler manner.

The present invention therefore relates to a process for the preparation of sugar ketals by reacting a sugar with a ketone in the presence of an acid catalyst, wherein A. the molecular boron trifluoride compound or trifluoromethanesulfonic acid is used in an amount of only from 0.01 to 10% by weight, based on the sugar used,
B. up to a 30-fold molar excess of the ketone is used, and
C. the water formed during the reaction is removed continuously from the reaction mixture.

The present invention relates in particular to a process for the preparation of diacetone-L-sorbose by reacting L-sorbose with acetone in the presence of an acid catalyst, wherein A. boron trifluoride diethyl etherate or trifluoromethanesulfonic acid is used in an amount of only from 0.01 to 10% by weight based on the sugar used,
B. up to a 30-fold molar excess of the ketone is used and
C. the water formed during the reaction is removed continuously from the reaction mixture.

In a particularly advantageous embodiment of the process, the boron trifluoride, the trifluoromethanesulfonic acid or, in general, a catalytic amount of a suitable acid catalyst is rendered ineffective under non-aqueous conditions when the reaction is complete, after which the ketone is distilled off and the reaction mixture is then worked up directly by fractional distillation. The process is particularly important for the reaction of L-sorbose with acetone to give 2,3:4,6-di-O-isopropylidene-L-sorbofuranose, which is required for the synthesis of ascorbic acid.

It is true that European Laid-Open Application No. 138,436 has disclosed a process for the ketalization of 2-ketogulonic acid, in which boron trifluoride diethyl etherate and trifluoromethanesulfonic acid are among the very large number of acidic ketalization catalysts mentioned. However, an α-ketosugar acid cannot be compared with ribose; furthermore, in inventions filed simultaneously or earlier by the same working group on the ketalization of sugars (cf. European Pat. Nos. 139,486, 76,118 or 91,223), only very specific ketalization catalysts, such as $SbCl_5$, $SbF_5$, HI, $CuCl_2$ or $CuBr_2$, have been stated to be useful, and furthermore only in catalytic amounts.

The following sugars can be ketalized with the aid of the novel process: pentoses such as ribose, arabinose, xylose, lyxose, ribulose or xylulose; hexoses, such as glucose, mannose, gulose, idose, galactose, fructose or sorbose; deoxysugars, such as rhamnose, 2-deoxyglucose or 2-deoxyribose, and sugar alcohols, such as ribitol, mannitol or sorbitol.

Suitable ketones for the novel process are acyclic ketones, such as acetone, methyl ethyl ketone, diethyl ketone, dipropyl ketones and dibutyl ketones, and cyclic ketones, such as cyclopentanone, cyclohexanone and cycloheptanone. Of particular importance is the ketalization with acetone, which takes place with very good yields. Ketalizations with cyclic ketones, such as cyclohexanone, take place very generally with less good yields.

The amount of ketone to be used varies and depends on the particular compound. Whether a mono-, di- or triketal is to be formed, and whether this can be formed, must also be taken into account. As a rule, the ketone is used in a large molar excess, i.e. from more than 10 times to about 30 times the molar amount, preferably from about 20 to 25 times the molar amount. The ketone serves as a reactant and at the same time as a solvent. It is possible in general to dispense with the use of a solvent which increases the solubility of the sugar, eg. dioxane or dimethyl sulfoxide, with the result that working up of the reaction mixture becomes substantially simpler and hence cheaper. However, where fairly high-boiling ketones are used, eg. cyclohexanone, which boils at 156° C., it may be advantageous additionally to use a solvent which forms a lower-boiling azeotrope with this ketone, in order to avoid overheating in the reaction mixture. Examples of such solvents are methylene chloride and dimethoxyethane.

Boron trifluoride is used as the catalyst in the form of a molecular compound with an ether, a carboxylic acid, a dialkyl sulfide or hydrogen fluoride, preferably as boron trifluoride diethyl etherate.

The boron trifluoride etherate or trifluoromethanesulfonic acid is used as the catalyst in a catalytic amount. The amount should be from 0.1 to 10, preferably from 1 to 5, % by weight, based on the weight of the sugar used as a starting material. Surprisingly, when larger amounts of boron trifluoride are used, the resulting yields are substantially lower.

To carry out the novel process, a mixture consisting of the sugar to be ketalized, the ketone and the $BF_3$ complex or the trifluoromethanesulfonic acid is refluxed. Depending on the type of reactants employed and the pressure selected, the reaction temperature is from about 20° to 150° C. under atmospheric or reduced pressure.

Various methods are known for removing the water formed during the reaction from the reaction mixture. For example, the condensate formed under reflux conditions and essentially consisting of the ketone and the water of reaction can be dried in the reaction vessel prior to being refluxed. This can be carried out very advantageously by, for example, connecting a Soxhlet extractor filled with a molecular sieve between the reflux condenser and the reaction vessel. However, it is also possible to distil off the water-containing ketone and replace the ketone distilled off by dry ketone.

The water may also be removed by azeotropic distillation with an inert solvent which forms an azeotrope with water. Solvents which have a lower boiling point than the ketone being reacted are particularly suitable for this purpose. For the reaction with acetone, these are, for example, solvents having a boiling point of below 56° C., preferably from 30° to 50° C., such as methylene chloride, pentane or cyclopentane. The low-boiling solvent is advantageously used only in a small amount (about 50–100 ml per 500 ml of ketone) so that, at the beginning of the reaction, it is present essentially only in the upper part of the column and not in the actual reaction vessel and does not further reduce the solubility of the sugar in the ketone, which in any case is poor. Only when the solid sorbose has gone into solution does a larger amount of the azeotrope-forming inert solvent no longer present any problems in the reaction vessel.

The reaction times depend on the type of sugar being ketalized, the amount of catalyst and the other reaction conditions. It is from about 5 minutes to 10 hours, preferably from about 1 hour to 8 hours.

To isolate the sugar ketals, the reaction mixture is cooled in general to a temperature from about 20° to −30° C., the acid catalyst is rendered ineffective, for example by adding an aqueous $NaHCO_3$ solution, and the aqueous phase is extracted several times with a suitable extracting agent, such as benzene or toluene, which is removed by distillation from the resulting sugar ketal after the extract has been washed and dried.

In a particularly advantageous embodiment of the novel process, the boron trifluoride or the trifluoromethanesulfonic acid is rendered ineffective under non-aqueous conditions when the reaction is complete, after which the ketone is evaporated off and the residue is subjected to fractional distillation. This can be done, for example, by adding stoichiometric amounts of an alkali metal alcoholate, in particular sodium methylate or potassium methylate, or by reaction with appropriate amounts of ammonia, amines or other basic compounds or alkali metal or alkaline earth metal halides, such as NaF, LiF or $CaF_2$. The reaction mixture, if necessary after filtration, can then be evaporated down under reduced pressure, the ketone evaporated off and the residue subjected to fractional distillation.

In a particularly preferred embodiment of the novel process, the reaction mixture is worked up so that the boron trifluoride or the trifluoromethanesulfonic acid is rendered ineffective by adding about an equimolar amount of sodium methylate or potassium methylate and then distilling the reaction mixture, i.e. first the excess ketone and, where relevant, the solvent are distilled off from the reaction mixture, and then the crude product obtained is subjected to fractional distillation. This has the particular advantage that the working up procedure comprising extraction, washing and evaporation, which is expensive on an industrial scale, is dispensed with completely, and the desired product is obtained in good yield and especially in high purity.

We have found that the great advantages obtained when, in working up the reaction mixture, the boron trifluoride is rendered ineffective under non-aqueous conditions, in particular by adding a stoichiometric amount of an alkali metal alcoholate, the ketone is evaporated off and the reaction mixture is then subjected to fractional distillation are also obtained if the ketalization of the sugar is carried out in the presence of a suitable protic acid as an acid catalyst, provided that this is used only in a catalytic amount, i.e. from about 0.01 to about 10, preferably from about 1 to 5, % by weight, based on the sugar used. Examples of suitable protic acids are $H_2SO_4$, HI and organic sulfonic acids, such as p-toluenesulfonic acid.

The present invention therefore also relates to a process for the preparation of sugar ketals by reacting a sugar with a ketone in the presence of from 0.01 to 10, preferably from 1 to 5, % by weight, based on the sugar used, of a suitable protic acid as an acid catalyst, with continuous removal of the water formed during the reaction, wherein the protic acid is rendered ineffective under non-aqueous conditions when the reaction is complete by adding a stoichiometric amount of an alkali metal alcoholate, the ketone is evaporated off and the reaction mixture is then subjected to fractional distillation.

With the aid of the process according to the invention, sugar ketals, in particular 2,3:4,6-di-O-isopropylidene-L-sorbofuranose, which is required for the synthesis of ascorbic acid, can be prepared in a particularly advantageous manner.

EXAMPLE 1

A mixture of 15 g (833 millimoles) of anhydrous D-glucose, 0.38 ml (3.1 millimoles) of boron trifluoride diethyl etherate and 333 ml (4.54 moles) of acetone ($H_2O$ content <0.1%) was refluxed for 8 hours. 40 g of a molecular sieve (3 Å, from Grace GmbH) were present in a Soxhlet extractor between the flask and the reflux condenser. When the reaction was complete, the reaction mixture was cooled to −10° C., and 10 ml of dilute aqueous sodium bicarbonate solution were added. Thereafter, the acetone was distilled off under reduced pressure, the residue was taken up with 50 ml of water and the solution was extracted 3 times with 50 ml of toluene. The combined toluene phases were washed with a little water and dried over sodium sulfate, and the toluene was distilled off under reduced pressure to give 19.9 g (92%) of 1,2:5,6-di-O-isopropylidene-α-D-glucofuranose. After the product had been recrystallized from a 15:1 hexane/acetone mixture, its melting point was determined as 110°–112° C.

EXAMPLE 2

A mixture of 15 g (833 millimoles) of D-mannose, 0.38 ml of boron trifluoride etherate and 333 ml of acetone ($H_2O$ content <0.1%) was refluxed for 2.5 hours, the condensate being dried as described in Example 1. Working up by a method similar to that described in Example 1 gave 17.0 g (78%) of 2,3:5,6-di-O-isopropylidene-α-D-mannofuranose, which, after recrystallization from n-hexane, had a melting point of 122°–124° C.

EXAMPLE 3

A mixture of 20 g (111 millimoles) of D-galactose, 0.5 ml (4.1 millimoles) of boron trifluoride etherate and 400 ml (5.45 moles) of acetone was refluxed for 5.5 hours, the condensate being dried as described in Example 1. Working up by a method similar to that described in Example 1 gave 25.9 g (90%) of 1,2:3,4-di-O-isopropylidene-α-D-galactopyranose. Chromatography over silica gel (660, from Merck) using a 6:4 hexane/acetone mixture gave an oily product.

Elemental analysis ($C_{12}H_{20}O_6$): calculated (%) C 55.4, H 7.7; found (%) 55.5, 7.8.

EXAMPLE 4

A mixture of 15 g (833 millimoles) of L-sorbose, 0.38 ml of boron trifluoride etherate and 333 ml of acetone was refluxed for 6 hours. 40 g of a molecular sieve (3 Å) were present in a Soxhlet extractor between the flask and the reflux condenser. When the reaction was complete, the reaction mixture was cooled to −10° C., and 10 ml of aqueous sodium bicarbonate solution were added. Thereafter, the acetone was distilled off under reduced pressure, the residue was taken up in 200 ml of toluene, and the solution was extracted twice with 30 ml of 5% strength aqueous $NaHCO_3$ solution. This solution was then washed with 10 ml of dilute NaCl solution and dried over sodium sulfate, and the toluene was distilled off under reduced pressure to give 18.7 g (86%) of 2,3:4,6-di-O-isopropylidene-α-L-sorbofuranose. After the product had been recrystallized from hexane, its melting point was measured as 78°–79.5° C.

EXAMPLE 5

A mixture of 90 g of L-sorbose, 2.28 ml of boron trifluoride etherate and 2 liters of acetone was refluxed for 6 hours, 240 g of a molecular sieve (3 Å, from Grace GmbH) being present in a Soxhlet extractor between the reaction vessel and the reflux condenser. When the reaction was complete, the reaction mixture was cooled to 0° C., and 1.47 g of sodium methylate were added. Three similar reaction batches were combined, and the acetone was distilled off from the combihed mixture under reduced pressure to give 393 g of a residue, which was subjected to fractional distillation in a packed column under a pressure up to 0.4 bar. 268.1 g (68.8%) of 96–98% pure 2,3:4,6-di-O-isopropylidene-α-L-sorbofuranose and 35.0 g (9.0%) of product having a purity of 92% were obtained. 16.1 g (4.1%) of product remained in the column and could be recycled for further use.

EXAMPLE 6

A mixture of 12 g (666 millimoles) of sorbose, 0.5 ml (4.1 millimoles) of boron trifluoride etherate and 400 ml of acetone was refluxed for 3 hours and the condensate flowing back was dried, these steps being carried out similarly to Example 5. Working up as described in Example 4 gave 14.1 g (81%) of 2,3:4,6-di-O-isopropylidene-α-L-sorbofuranose.

EXAMPLE 7

A mixture of 20 g (111 millimoles) of sorbose, 2 ml (16.4 millimoles) of boron trifluoride etherate and 400 ml of acetone was refluxed for 4 hours, the condensate flowing back being dried as described in Example 1. When 0.4 g (10.5 millimoles) of sodium methylate were added and the mixture worked up as described in Example 5, 23.5 g (81%) of 2,3:4,6-di-O-isopropylidene-α-L-sorbofuranose were obtained.

EXAMPLE 8

A mixture of 20 g (133 millimoles) of D-arabinose, 0.5 ml (4.1 millimoles) of boron trifluoride etherate and 400 ml of acetone was refluxed for 2 hours, the condensate flowing back being dried as described in Example 1. Working up similarly to Example 1 gave 27.4 g (89%) of 98% pure 1,2:3,4-di-O-isopropylidene-β-D-arabinopyranose. After the product had been crystallized from n-hexane, its melting point was measured as 41°–41.5° C.

EXAMPLE 9

A mixture of 20 g of D-xylose, 0.5 ml of boron trifluoride etherate and 400 ml of acetone was refluxed for 4 hours, the condensate flowing back being dried as described in Example 1. Working up similarly to Example 1 gave 28.4 g (93%) of 96% pure 1,2:3,5-di-O-isopropylidene-α-D-xylofuranose. After the product had been recrystallized from n-hexane, its melting point was measured as 43°–45° C.

EXAMPLE 10

A mixture of 10 g (66.6 millimoles) of D-ribose, 0.25 ml of boron trifluoride etherate and 200 ml of acetone was refluxed for 5 minutes, the condensate flowing back being dried as described in Example 1. When the reaction was complete, 5 ml of aqueous sodium bicarbonate solution were added, and the acetone was distilled off under reduced pressure. The residue was then purified by chromatography over silica gel (G 60, from Merck) using a 3:2 hexane/acetone mixture. 7.8 g (62%) of 2,3-isopropylidene-D-ribofuranose were obtained.

Elemental analysis ($C_8H_{14}O_5$). calculated (%) C 50.5, H 7.4; found 50.6, 7.5.

EXAMPLE 11

A mixture of 20 g of D-mannitol, 0.5 ml of boron trifluoride etherate and 400 ml of acetone was refluxed for 4 hours, the condensate flowing back being dried as described in Example 1. Working up similarly to Example 1 gave 31.5 g (95%) of 97% pure 1,2:3,4:5,6-tri-O-isopropylidene-D-mannitol. After the product had been recrystallized from n-hexane, its melting point was measured as 69°–70° C.

EXAMPLE 12

A mixture of 20 g of D-fructose, 0.5 ml of boron trifluoride etherate and 400 ml of acetone was refluxed for 3.5 hours, the condensate flowing back being dried as described in Example 1. When the reaction was complete and working up had been carried out as in Example 1, 26.3 g (91%) of 2,3:4,6-di-O-isopropylidene-β-D-fructopyranose were obtained. After the product had been recrystallized from n-hexane, its melting point was measured as 96°–98° C.

EXAMPLE 13

A mixture of 5 g of D-arabinose, 0.13 ml of boron trifluoride diethyl etherate, 75 ml of cyclohexanone and 60 ml of dichloromethane was refluxed for 90 minutes. 20 g of a molecular sieve were present in a Soxhlet extractor between the flask and the reflux condenser. When the reaction was complete, the reaction mixture was cooled to +20° C., diluted with 150 ml of toluene, extracted with aqueous NaHCO$_3$ solution, washed with water and dried over Na$_2$SO$_4$. The solvent mixture was distilled off under reduced pressure to give 9.8 g (95%) of 1,2:3,4-di-O-cyclohexylidene-β-D-arabinopyranose. After the product had been recrystallized from n-hexane, its melting point was measured as 71.5°–73° C.

EXAMPLE 14

A mixture of 10 g of anhydrous D-glucose, 0.25 ml of boron trifluoride diethyl etherate, 150 ml of dimethoxyethane and 50 ml of cyclohexanone was refluxed for 80 minutes. After carrying out the reaction and working up as described in Example 13, and recrystallization from n-hexane, 7.5 g (40%) of 1,2:5,6-di-O-cyclohexylidene-α-D-glucofuranose of melting point 133.5°–135° C. were obtained.

EXAMPLE 15

A mixture of 20 g of L-sorbose, 0.5 ml of boron trifluoride diethyl etherate, 100 ml of cyclohexanone and 300 ml of dimethoxyethane was refluxed for 25 minutes. After carrying out the reaction and working up as described in Example 13, and recrystallization from n-hexane, 16.6 g (44%) of 2,3:4,6-di-O-cyclohexylidene-α-L-sorbofuranose of melting point 122°–123.5° C. were obtained.

EXAMPLE 16

A mixture of 20 g of L-sorbose, 400 ml of acetone and 0.5 ml of boron trifluoride diethyl etherate was refluxed in an apparatus consisting of a three-necked flask, a packed column, a water separator and a reflux condenser. 70 ml of n-pentane were added via the water separator, this amount being such that the n-pentane was present only in the vapor space and not in the reaction space. After 3 hours, a further 50 ml of n-pentane were added, and refluxing was continued for a further 12 hours at a bottom temperature of 50° C. 5.8 ml of a lower phase containing 62.5% by weight of water were obtained in the water separator during this procedure.

When the reaction was complete, the reaction mixture was cooled to 10° C. and 0.33 g of sodium methylate was added. Thereafter, the acetone was distilled off under reduced pressure, the residue was taken up in 100 ml of toluene, the solution was extracted twice with 10 ml of 5% strength NaHCO$_3$ solution, washed with 5 ml of 5% strength NaCl solution and dried over Na$_2$SO$_4$, and the toluene was distilled off under reduced pressure to give 24.7 g (85.5%) of 2,3:4,6-di-O-isopropylidene-α-L-sorbofuranose.

EXAMPLE 17

A mixture of 20 g (111 millimoles) of L-sorbose, 200 μl (2.3 millimoles) of trifluoromethanesulfonic acid (TFMSA) and 400 ml of acetone (H$_2$O content 0.1%) was refluxed for 4.5 hours. 40 g of a molecular sieve (3 Å) were present in a Soxhlet extractor between the reaction flask and the reflux condenser. When the reaction was complete, the reaction mixture was cooled to −10° C. and 10 ml of aqueous NaHCO$_3$ solution were added. Thereafter, the acetone was distilled off under reduced pressure, the residue was taken up in 35 ml of H$_2$O and the solution was extracted with 3 times 110 ml of toluene at 70° C. The combined toluene phases were washed with 7.5 ml of H$_2$O and dried over Na$_2$SO$_4$, and the toluene was distilled off under reduced pressure to give 24.7 g (85.5%) of 2,3:4,6-di-O-isopropylidene-α-L-sorbofuranose (DAS). After the product had been recrystallized from toluene, its melting point was measured as 78°–79° C.

EXAMPLE 18

A mixture of 20 g (111 millimoles) of L-sorbose, 100 μl (1.1 millimoles) of TFMSA and 400 ml of acetone was refluxed for 2.5 hours, the condensate flowing back being dried as described in Example 1. After the mixture had been cooled and neutralized and the acetone distilled off, the residue was taken up in 300 ml of toluene, the solution was extracted at room temperature with 15 ml of 5% strength aqueous $NaHCO_3$ solution and 15 ml of $H_2O$ and dried over $Na_2SO_4$, and the toluene was distilled off to give 24.8 g (85.7%) of DAS.

EXAMPLE 19

A mixture of 20 g (111 millimoles) of L-sorbose, 10 μl (0.11 millimole) of TFMSA and 400 ml of acetone was refluxed for 7 hours as described in Example 1. The reaction mixture was cooled to −10° C., after which 1 ml of concentrated aqueous $NH_4OH$ solution was added, the mixture was filtered, the acetone was then distilled off and the residue was taken up in 300 ml of toluene. Working up was continued as described in Example 2, 24.1 g (83.3%) of DAS being obtained.

EXAMPLE 20

A mixture of 30 g of L-sorbose, 600 ml of acetone and 15 μl of TFMSA was refluxed in an apparatus consisting of a three-necked flask, a packed column, a water separator and a reflux condenser. 75 ml of cyclopentane were added via the water separator. After 6 hours, a further 100 ml of cyclopentane were added, and refluxing was continued for a further 18 hours. A total of 10.5 ml of a lower phase containing 51% by weight of $H_2O$ was obtained in the water separator. When the reaction was complete, the reaction mixture was cooled to 0° C. and 500 μl of 5% strength $NaOCH_3/CH_3OH$ solution were added. The mixture was evaporated down, the residue was taken up in 450 ml of toluene, and the solution was washed with 15 ml of $NaHCO_3$ solution and 10 ml of $H_2O$, dried and evaporated down to give 40.3 g (93.0%) of DAS.

EXAMPLE 21

A mixture of 90 g of L-sorbose, 45 μl of TFMSA and 1,800 ml of acetone was refluxed for 12 hours, 180 g of a molecular sieve being used for drying the condensate. When the reaction was complete, the reaction mixture was cooled to 0° C. and 1 ml of 5% strength $NaOCH_3/CH_3OH$ solution was added. The reaction products from four similar reaction batches were combined, and the acetone was distilled off from the combined batches to give 535 g of residue, 470 g of which were subjected to fractional distillation under 0.1–0.25 mbar in a packed column. 306 g (67.0%) of 96–97.5% pure DAS and 45 g (9.9%) of 94% pure product were obtained, while 30.5 g (6.7%) of product remained in the column.

We claim:
1. A process for the preparation of a sugar ketal by reacting a sugar with a ketone in the presence of an acid catalyst, wherein
   A. a molecular boron trifluoride compound or trifluoromethanesulfonic acid is used in an amount of from 0.01 to 10% by weight, based on the sugar used,
   B. more than 10 to about 30-fold molar excess of the ketone is used and
   C. the water formed during the reaction is removed continuously from the reaction mixture.
2. A process for the preparation of diacetone-L-sorbose by reacting L-sorbose with acetone in the presence of an acid catalyst, wherein
   A. boron trifluoride diethyl etherate or trifluoromethanesulfonic acid is used in an amount of from 0.01 to 10% by weight, based on the sugar used,
   B. more than 10 to about a 30-fold molar excess of the ketone is used and
   C. the water formed during the reaction is removed continuously from the reaction mixture.
3. A process for the preparation of a sugar ketal as claimed in claim 1 by reacting a sugar with a ketone in the presence of a molecular boron trifluoride compound as an acid catalyst, wherein boron trifluoride diethyl etherate is used in an amount of from 0.01 to 10% by weight, based on the sugar used.
4. A process for the preparation of a sugar ketal as claimed in claim 3, wherein a pentose, a hexose, a deoxysugar or a sugar alcohol is used as the sugar.
5. A process for the preparation of a sugar ketal as claimed in claim 1, wherein the sugar used is L-sorbose.
6. A process for the preparation of a sugar ketal as claimed in claim 1, wherein the ketone used is acetone.
7. A process for the preparation of a sugar ketal as claimed in claim 6, wherein a solvent which increases the solubility of the sugar is not used in said process.
8. A process for the preparation of a sugar ketal as claimed in claim 1, wherein water is removed from the reaction mixture by azeotropic distillation with the aid of an inert solvent having a boiling point below 56° C.
9. A process for the preparation of a sugar ketal as claimed in claim 1, wherein the water is removed from the refluxing reaction mixture by drying the condensate, which essentially consists of the ketone and water, before it flows back into the reaction vessel.
10. A process for the preparation of a sugar ketal as claimed in claim 1, wherein, when the reaction is complete, the boron trifluoride or the trifluoromethanesulfonic acid is rendered ineffective by adding about an equimolar amount of sodium methylate, after which the ketone is evaporated off and the reaction mixture is subjected to fractional distillation.
11. A process for the preparation of a sugar ketal as claimed in claim 3, wherein
   A. boron trifluoride is used in the form of a boron trifluoride diethyl etherate,
   B. the ketone used is acetone, and a solvent which increases the solubility of the sugar is not used in said process, and
   C. the water formed during the reaction is removed continuously from the reaction mixture by azeotropic distillation with the aid of an inert solvent having a boiling point below 56° C.
12. A process for the preparation of diacetone-L-sorbose by reacting L-sorbose with acetone, as claimed in claim 2, wherein
   A. trifluoromethanesulfonic acid is used as the acid catalyst, in an amount of from 0.01 to 10% by weight, based on the sorbose used,
   B. more than 10% to about a 30-fold molar excess of acetone is used and
   C. the water formed during the reaction is removed continuously from the reaction mixture.

13. A process for the preparation of diacetone-L-sorbose by reacting L-sorbose with acetone, as claimed in claim 12, wherein a solvent which increases the solubility of the sugar is not used in said reaction, and the water formed during the reaction is removed continuously from the reaction mixture by azeotropic distillation with the aid of an inert solvent having a boiling point below 56° C.

14. A process for the preparation of diacetone-L-sorbose by reacting L-sorbose with acetone, as claimed in claim 12, wherein, when the reaction is complete, the trifluoromethanesulfonic acid is rendered ineffective by adding about an equimolar amount of sodium methylate, after which the ketone and the inert solvent are evaporated off and the reaction mixture is subjected to fractional distillation.

* * * * *